(12) United States Patent
Pelagatti et al.

(10) Patent No.: US 8,882,894 B2
(45) Date of Patent: Nov. 11, 2014

(54) VAPORISATION INJECTOR

(75) Inventors: Stefano Pelagatti, Rodano (IT); Eric Phillips, Austin, TX (US); Paolo Magni, Rodano (IT)

(73) Assignee: Thermo Fisher Scientific S.p.A., Rodano (MI) (IT)

( * ) Notice: Subject to any disclaimer, the term of this patent is extended or adjusted under 35 U.S.C. 154(b) by 238 days.

(21) Appl. No.: 13/518,761

(22) PCT Filed: Feb. 1, 2010

(86) PCT No.: PCT/IT2010/000030
§ 371 (c)(1),
(2), (4) Date: Jul. 20, 2012

(87) PCT Pub. No.: WO2011/092724
PCT Pub. Date: Aug. 4, 2011

(65) Prior Publication Data
US 2012/0280061 A1 Nov. 8, 2012

(51) Int. Cl.
| *B01D 53/02* | (2006.01) |
| *G01N 30/12* | (2006.01) |
| *G01N 30/10* | (2006.01) |
| *G01N 30/04* | (2006.01) |
| *G01N 30/16* | (2006.01) |
| *G01N 30/18* | (2006.01) |

(52) U.S. Cl.
CPC ............... *G01N 30/12* (2013.01); *G01N 30/10* (2013.01); *G01N 30/04* (2013.01); *G01N 30/16* (2013.01); *G01N 2030/167* (2013.01); *G01N 30/18* (2013.01); *G01N 2030/185* (2013.01)
USPC ........ 96/105; 96/101; 95/87; 95/89; 73/23.41

(58) Field of Classification Search
CPC ....... G01N 30/04; G01N 30/10; G01N 30/16; G01N 30/18; G01N 2030/167; G01N 2030/185
USPC ............ 96/101, 105; 95/82, 87, 89; 73/23.35, 73/23.41
See application file for complete search history.

(56) References Cited

U.S. PATENT DOCUMENTS

| 5,827,353 | A  | * | 10/1998 | O'Neil ............................... 95/87 |
| 5,944,877 | A  | * | 8/1999  | O'Neil ............................ 96/101 |
| 7,273,518 | B2 | * | 9/2007  | Song et al. ...................... 96/105 |
| 2006/0065122 | A1 |   | 3/2006  | Song et al. |

FOREIGN PATENT DOCUMENTS

| EP | 0 510 511 A2 | 10/1992 |
| EP | 0 551 847 A1 | 7/1993 |
| EP | 1 063 523 A2 | 12/2000 |
| FR | 2 928 733 A1 | 9/2009 |
| JP | 2003 344374 A | 12/2003 |

* cited by examiner

*Primary Examiner* — Robert Clemente
(74) *Attorney, Agent, or Firm* — Lucas & Mercanti, LLP

(57) ABSTRACT

The invention relates to a vaporization injector for a gas chromatograph, said injector comprising a structure (11) mounted in a detachable manner on the gas chromatograph body and including the sample introduction means, the vaporization chamber and pneumatic connections for feeding the carrier gas to the vaporization chamber and to the septum purge means, as well as pneumatic connections for evacuating the splitted sample and carrier gases.

15 Claims, 6 Drawing Sheets

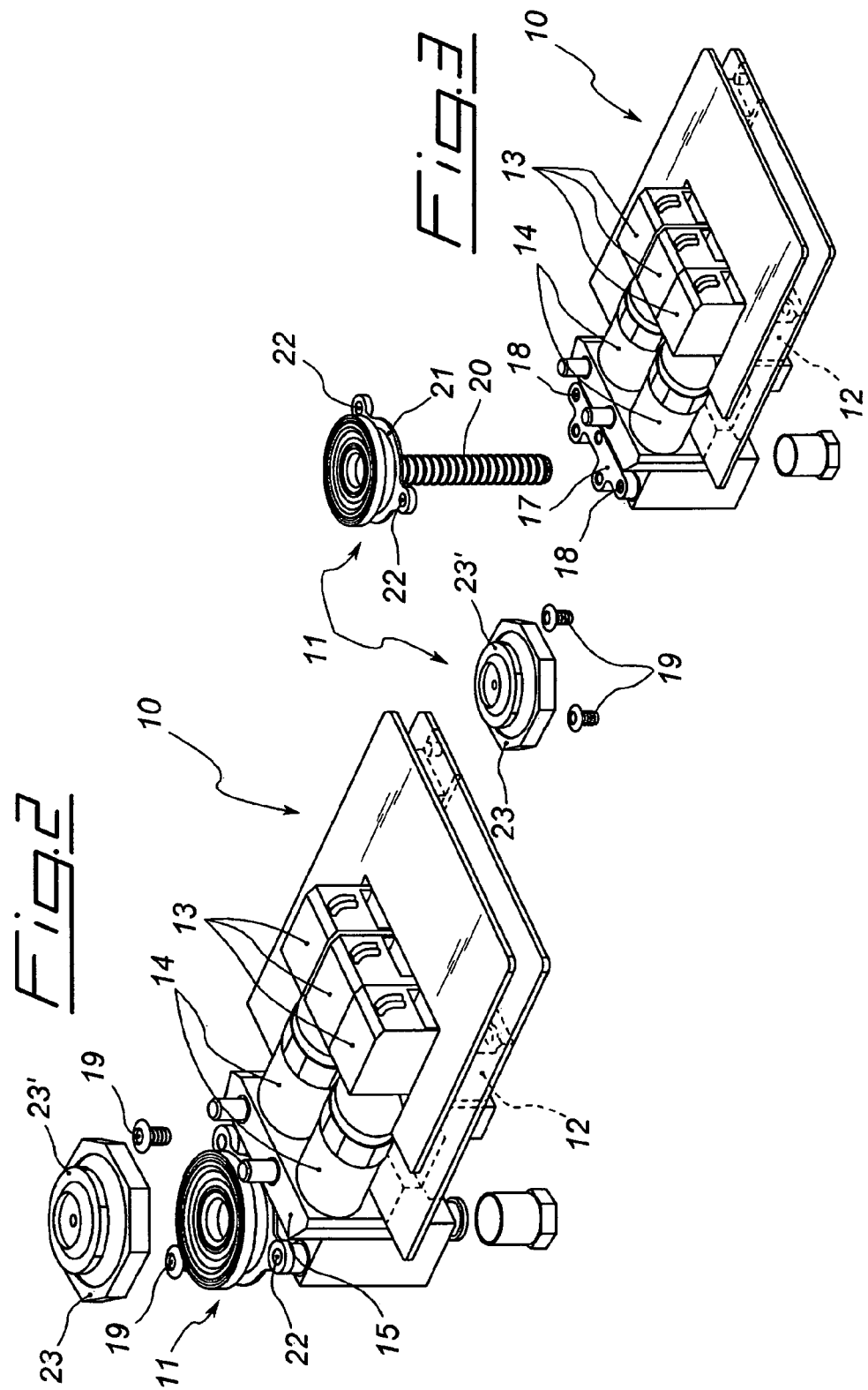

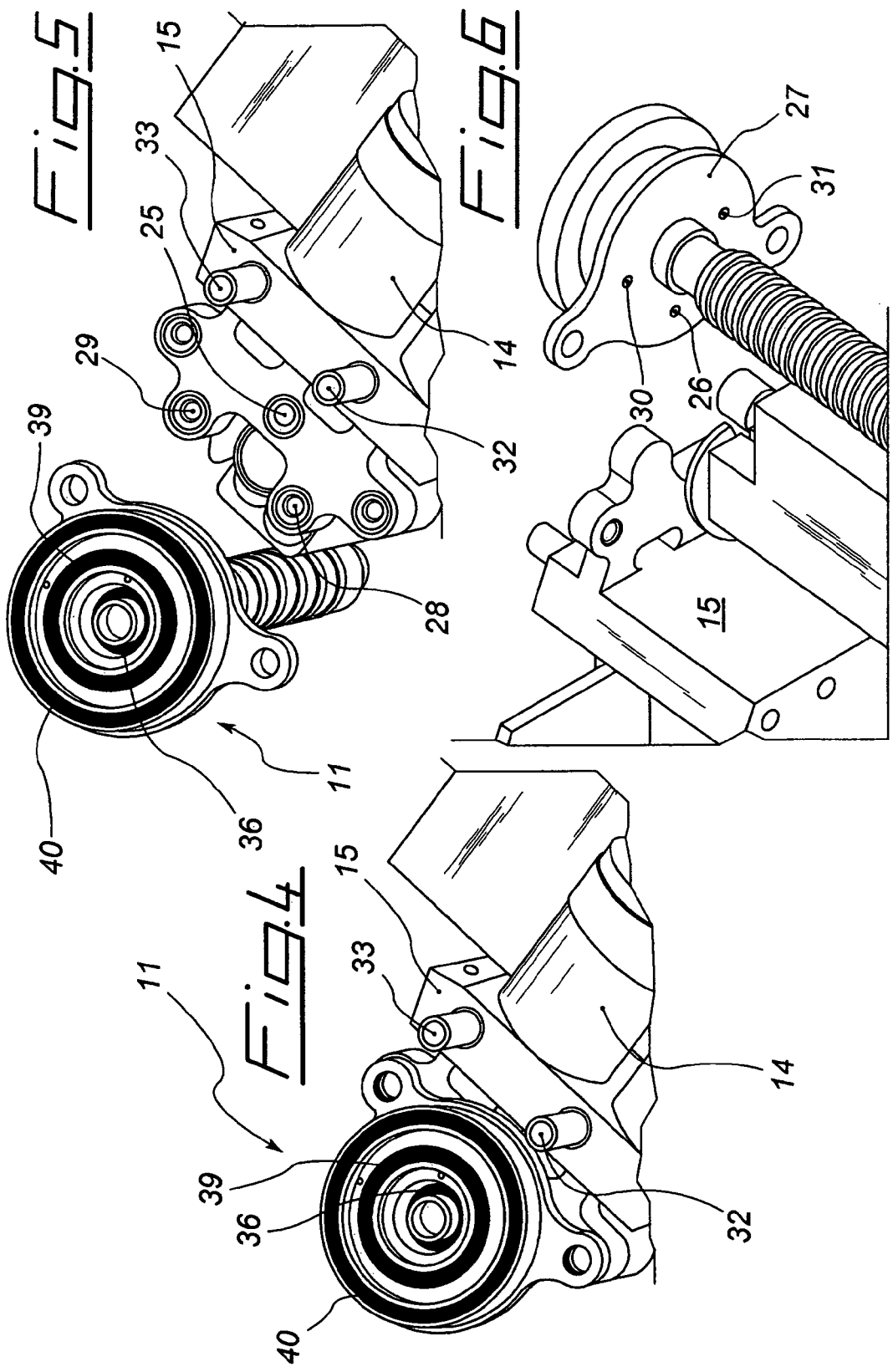

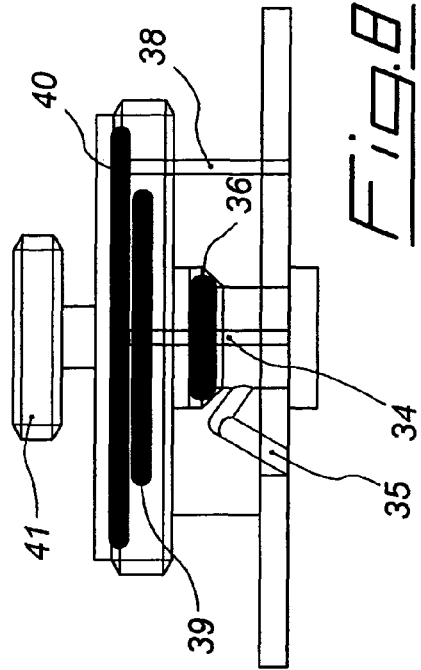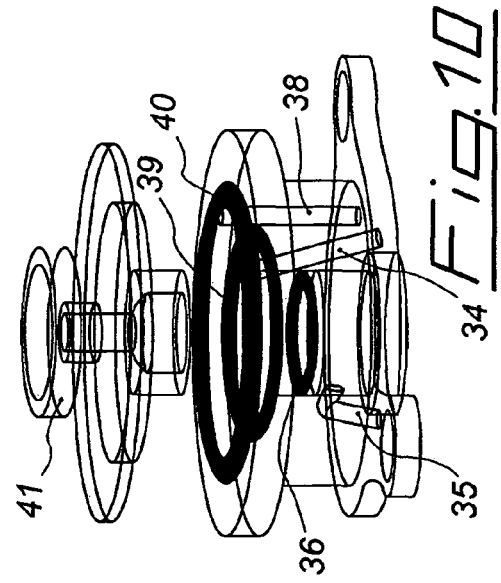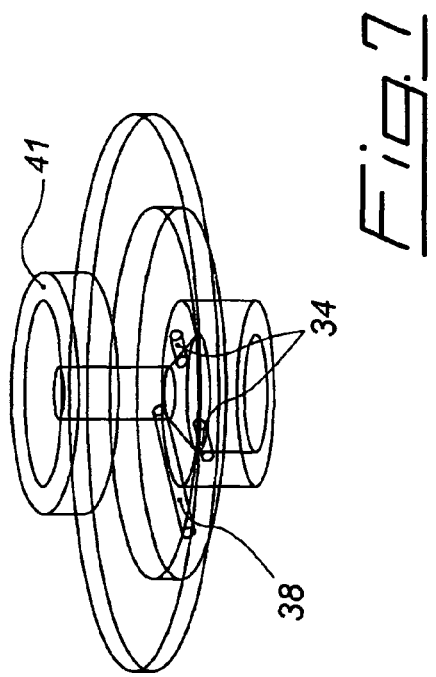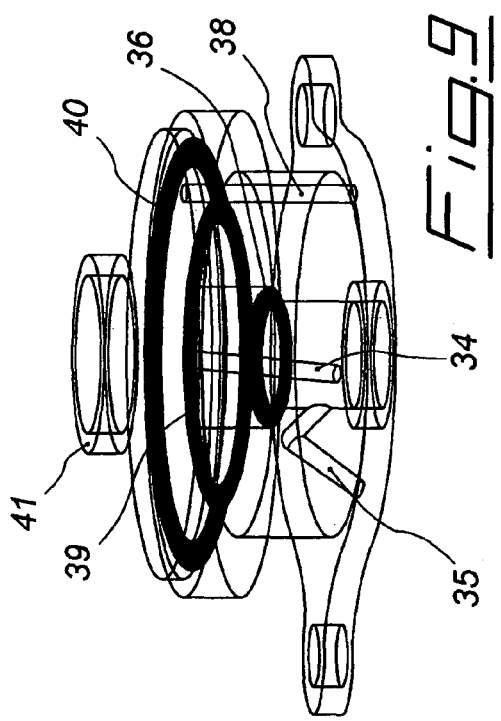

VAPORISATION INJECTOR

CROSS-REFERENCE TO RELATED APPLICATION

This application is a 371 of PCT/IT2010/000030, filed Feb. 1, 2010, the contents of which are incorporated herein by reference.

BACKGROUND OF THE INVENTION

The present invention concerns a vaporisation injector suitable for operating in a gas chromatography instrument.

The injector is a device which allows the transfer of a sample, consisting of the substance to be analysed and a solvent, for example from a syringe to the gas chromatography column by means of a carrier gas. The injectors can be on-column injectors, when the sample is injected into the column in a liquid form and vaporises at the beginning of the column, or they can be vaporisation injectors, in which case the sample is heated and vaporised inside the injector.

The subject of the present invention is a vaporisation injector, generally consisting of a heated vaporisation chamber into which the sample is fed for example via the needle of a syringe which crosses an insulation septum.

From the vaporisation chamber, the vaporised sample is transferred to the column by the action of the carrier gas, said transfer being performed on the whole sample injected (splitless), or only on a fraction of the sample injected (split). In the latter case the main part of the sample is diverted and discharged together with a fraction of the carrier gas. Furthermore, a current of the carrier gas is diverted before it meets the sample, in order to purge the septum.

DESCRIPTION OF THE PRIOR ART

Therefore, a vaporisation injector with splitting of the sample must also have, in addition to the means for heating the vaporisation chamber, suitable pneumatic connections to subdivide the carrier between the inlet into the vaporisation chamber and a duct for purging of the septum, and to subdivide the flow of the carrier and the sample between the part sent to the column and the part which is diverted or splitted.

In the evolution of these injectors the three different lines described above are controlled by proportional valves, preferably acting on one single manifold, the septum is mounted so that it can be replaced and the inside surface of the vaporisation chamber is covered by a liner which can also be removed for cleaning or replacement.

Non-vaporisable parts of the sample and fragments of septum can accumulate in the injector in the long term, negatively affecting the subsequent analyses, also in the event of replacement of the liner and/or septum. Although the majority of the contaminants remain on the liner, part of them tend to accumulate on the bottom, inside the injector body. The splitting line is also subject to contamination by the sample which can even clog it, and for this reason a carbon filter is provided. Said filter, however, cannot treat the line between the injector and the filter, which thus becomes a trap for the heaviest compounds.

The injectors produced so far, with relative pneumatic system, are fixedly mounted on the body of the gas chromatograph and hence maintenance can be performed only at the level of the septum, the liner and the carbon filter which can be installed on the carrier, purging and/or splitting lines. Therefore, the contamination of the other parts of the injector, injector body and pneumatic system cannot be removed unless the injector is entirely replaced.

OBJECTS OF THE INVENTION

The object of the invention is to provide a vaporisation injector which can be easily and rapidly disassembled, like the liner, to allow cleaning, for example by sonication or other known processes, or replacement of parts.

A further object of the invention is to provide a pneumatic system which allows disassembly of the injector and furthermore permits the installation of filters in particularly convenient and accessible positions for maintenance or replacement, while maintaining total system efficiency.

SUMMARY OF THE INVENTION

In order to achieve these and other objects, the invention concerns a vaporisation injector having the characteristics and construction features as described in the claims.

BRIEF DESCRIPTION OF THE DRAWINGS

A preferred embodiment of the invention will now be illustrated with reference to the accompanying drawings, in which:

FIGS. 2 and 3 illustrate in perspective the conformation and modes of removal of the injector body from the above-mentioned block.

FIGS. 4, 5 and 6 illustrate, again in perspective, the arrangement of the apertures for inlet and outlet of the gases and the arrangement of the seals in the injector body.

FIGS. 7 to 10 illustrate, in different perspective views, the arrangement of the gas channels inside the injector body.

DESCRIPTION OF THE PREFERRED EMBODIMENTS

Figure 1:
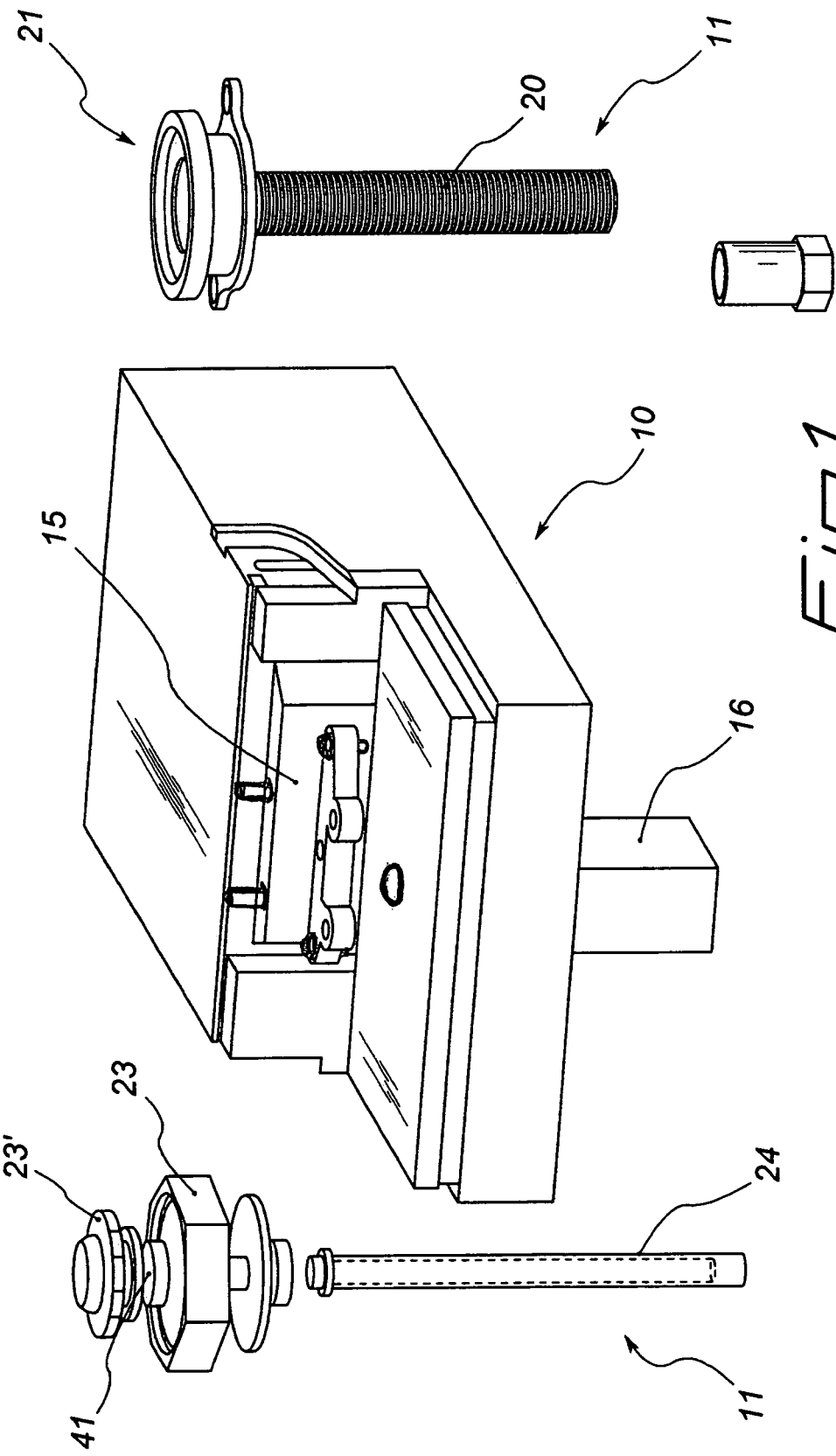
FIG. 1 illustrates in perspective the injector body, disassembled from the relative block of a gas chromatograph, housing the heating means, the electronics and the manifold of the pneumatic system.

The injector shown in FIGS. 1 to 3 is essentially composed of a fixed part, the components of which can nevertheless be disassembled, here called "block" and indicated in general by reference number 10, and a removable part 11, which constitutes the injector body.

The block 10 comprises the control electronics 12, the control valves 13 of the pneumatic system; the filters 14 and a manifold 15 for distribution of the incoming carrier gas and the outgoing splitting and purge gases, in addition to the means 16 for controlled heating of the injector body, the structure of these components being essentially known in the field.

The body 10 furthermore defines a surface 17 designed to support the body 11 of the injector and having two threaded apertures 18 for housing screws 19 for fastening the injector body.

The injector body 11 consists of a cylindrical element 20 designed to be inserted in the heating element 16 and terminating at the top in a wider area 21 comprising a counter-surface resting on the surface 17 of the block, with apertures 22 for the screws 19, in addition to the gas distribution means which will be described below.

At the top, the injector body 11 has an upper closing nut 23 to permit access to the vaporisation chamber where a liner 24 can be housed and removed for replacement or cleaning. However, due to the possibility to remove the injector body, a liner is not strictly required. A further nut 23' is also provided for removing the upper cover, containing the injection hole, in order to allow access to the support 41 of the septum so that it can be removed for cleaning or replacement.

FIGS. 4 to 10 illustrate details of the injector pneumatic system. The carrier gas is fed to the manifold 15, which feeds it to the aperture 25 provided on the fixed surface 17 connected to a corresponding aperture 26 presented by the counter-surface 27 of the injector body. The surface 17 also has two further apertures 28 and 29 which connect to corresponding apertures 30 and 31 on the injector body. The apertures 28, 31 and 29, 30 are provided respectively for outlet of the splitting gas and for outlet of the purge gas, which are conveyed to the outside, via the mouths 32 and 33. The apertures 25, 28 and 29 are provided with seals, for example in the form of O-rings.

Inside the injector body, passages are provided for the transit gases and O-rings for separation of the flows, as can be seen in FIGS. 7 to 10 in particular. More specifically, the carrier gas which enters the injector body is sent, via the channels indicated by 34 in FIGS. 7-10, to the cover of the liner 24, from where it is fed to the inside of the liner 24 and, partly, to the injector head to purge the septum.

The carrier gas and sample flow which is not sent to the column (splitting flow) is conveyed back towards the head of the injector on the outside of the liner 24 and fed to a discharge channel 35 and to the apertures 31 and 28.

The separation between the carrier gas and the splitting gas is obtained by means of a first toroidal gasket (O-ring) 36. The gas coming from cleaning of the septum (purge flow) is sent to the apertures 30 and 29 through the channels indicated by 38 and said flow is separated from the carrier flow by means of a second toroidal gasket (O-ring) 39 in the injector head. Lastly, a third toroidal gasket 40 separates the purge gas from the external atmosphere.

The flows are controlled, according to known methods, by pressure sensors and proportional valves, installed on the block 10.

Figure 11:
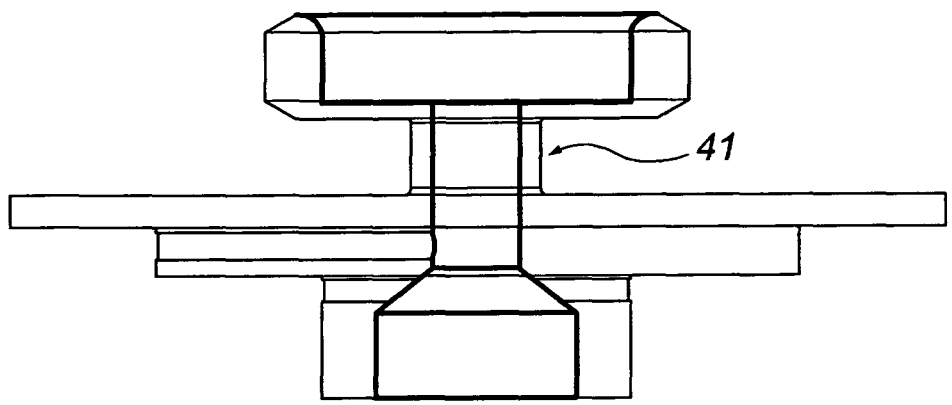
FIGS. 11 and 12 are axial sections of the septum supporting head in two versions which can be replaced or modified.
Figure 12:
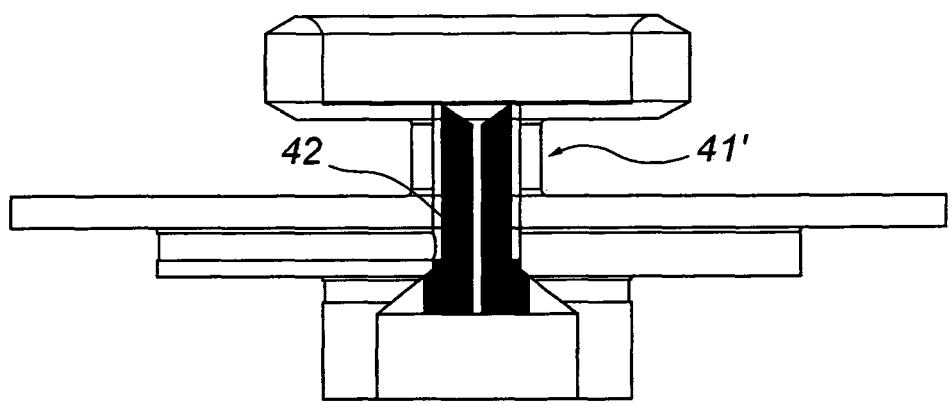

With reference to FIGS. 11 and 12, the head 41 supporting the septum can be provided and applied in two different versions. More specifically, FIG. 11 illustrates a supporting head in which the injection needle does not come into contact with the hot inner surface of the injector, i.e. to carry out the so-called cold needle injection technique.

In FIG. 12 the supporting head 41' of the septum, which can be similar to that of FIG. 11 and therefore replaces it, or is different from that of FIG. 11 with some modifications, has an insert 42, applied previously or which can be inserted, to reduce the diameter of the needle passage, permitting local heating of the latter, in order to carry out the so-called hot needle injection technique. Alternatively, again for hot needle injections, it is possible to simply replace the supporting head 41 of FIG. 11 with the same type of supporting head but having a narrower channel for passage of the needle.

Figure 13:
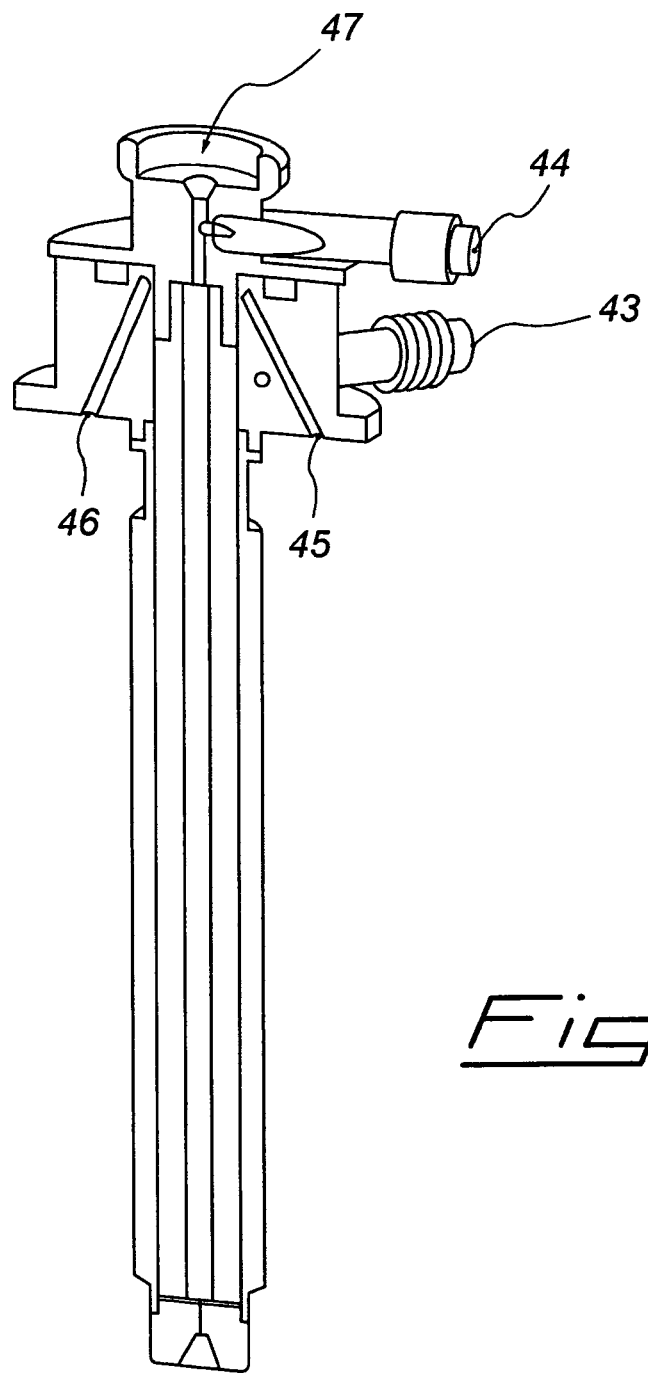
FIG. 13 shows, in an axial section, an embodiment form of the injector adapted for introduction of gaseous samples.

FIG. 13 shows an embodiment of the injector which is able to allow the introduction of gas samples, for instance as obtained from a purge and trap sampler or a thermal desorber. The injector body comprises a gas connector 43 for the introduction of the carrier and a second gas connector 44 for the introduction of the gaseous sample. The purge line 45 and split line 46 are also shown. Of course in case of a gas sampling the upper aperture 47 for the introduction of a syringe needle should be closed, for instance by a septum.

The invention claimed is:

1. A vaporization injector for gas chromatographs, comprising a fixed part constituting a block and a removable part constituting an injector body, designed to receive an injected sample, directly or in a replaceable liner, said injector body comprising:
    a housing head for a replaceable septum, having a detachable covering element, and
    means for the supply of carrier gas and/or for the evacuation of splitting gas and/or purge gas from the septum,
    wherein:
    a) said injector body having a counter-surface and being mounted with said counter-surface on a surface of said block in a detachable manner;
    b) said gas supply and evacuation means including (i) channels disposed in said injector body and a plurality of apertures disposed on said counter surface of said injector body in communication with said channels, and (ii) a plurality of apertures disposed on said surface of said block, whereby said apertures of said injector body coincide and are in communication with said apertures of said block surface;
    c) pneumatic seals are provided at the interface between the coinciding apertures of said injector body and those of said block; and
    d) pneumatic seal means are provided to separate the paths of the gases inside said injector body.

2. An injector as claimed in claim 1, wherein said block has a seat for housing said injector body in an insertable and removable manner, said block comprising fixed means for controlled heating of a vaporization chamber or said liner.

3. An injector as claimed in claim 2, wherein said seat for housing said injector body is provided with detachable fixing means for said injector body in the operating condition.

4. An injector as claimed in claim 3, wherein said seat for housing said injector body has a surface suitable for coupling with a corresponding surface of said injector body, said apertures for supply and evacuation of the gases fed to and coming from said injector body leading to said surfaces.

5. An injector as claimed in claim 4, wherein said block comprises a manifold, a plurality of valves and one or more filters for control of the gas flows, said manifold, valves and filters being mounted in a detachable manner for replacement or cleaning.

6. An injector as claimed in claim 4, wherein said injector body has, inside, a first channel for supplying the carrier gas from said surface inside said injector body itself towards said vaporization chamber or liner.

7. An injector as claimed in claim 6, wherein part of the carrier gas fed into said injector body is diverted towards the septum, for purging the same, said injector body having a second channel for conveying the purge gas to the outside of said injector body.

8. An injector as claimed in claim 6, wherein said injector body has a third channel for conveying the splitting gas to the outside of said injector body itself.

9. An injector as claimed in claim 1, wherein said injector body comprises a closing cover supporting said septum housing head which can be fixed in a removable manner to the body of said injector body to close a central cavity to which said channels of said injector body lead, at least partly.

10. An injector as claimed in claim 9, wherein said central cavity houses gaskets for separating the gas flows from each other and from the outside atmosphere.

11. An injector as claimed in claim 10, wherein said gaskets are of the O-ring type.

12. An injector as claimed in claim 1, wherein the septum housing head has an internal passage for the needle of sufficiently large diameter to avoid local heating of the needle itself during injection.

13. An injector as claimed in claim 1, wherein the septum housing head can be replaced with a head having an internal passage for the needle of sufficiently small diameter to allow local heating of the needle itself during injection.

14. An injector as claimed in claim 1, wherein the septum housing head involves a seat for an insert defining an internal passage for the needle of sufficiently small diameter to allow local heating of the needle itself during injection.

15. An injector as claimed in claim 1, wherein a gaseous sample feeding duct is provided in the upper part of said injector body and means are disposed in said injector body upper part for closing a needle introduction aperture.

* * * * *